United States Patent [19]

Murakoshi et al.

[11] Patent Number: 4,562,831
[45] Date of Patent: Jan. 7, 1986

[54] ENDOSCOPE SYSTEM USING SOLID STATE IMAGING DEVICE

[75] Inventors: Makoto Murakoshi, Tokyo; Kunio Ando, Omiya, both of Japan

[73] Assignees: Fuji Photo Film Co. Ltd., Kanagawa; Fuji Photo Optical Co. Ltd., Saitama, both of Japan

[21] Appl. No.: 444,387

[22] Filed: Nov. 26, 1982

[30] Foreign Application Priority Data

Dec. 14, 1981 [JP] Japan ................ 56-201371

[51] Int. Cl.$^4$ ............................................ A61B 1/06
[52] U.S. Cl. ............................................ 128/6; 358/98
[58] Field of Search ........................................ 128/4–8, 128/23, 665; 358/42, 98, 110, 113, 253, 213, 44, 75; 362/32, 166–168, 293

[56] References Cited

U.S. PATENT DOCUMENTS

| | | | |
|---|---|---|---|
| 3,527,974 | 9/1970 | Cooper | 313/113 |
| 3,887,279 | 6/1975 | Rubin | 356/404 |
| 4,170,987 | 10/1979 | Anselmo et al. | 358/113 |
| 4,242,703 | 12/1980 | Tsuboshima et al. | 358/44 |
| 4,245,241 | 1/1981 | Sato et al. | 358/44 |
| 4,253,447 | 3/1981 | Moore et al. | 358/98 |
| 4,343,300 | 8/1982 | Hattori | 128/6 |
| 4,403,247 | 9/1983 | Sone et al. | 358/44 |
| 4,404,585 | 9/1983 | Hjortzberg | 358/42 |

Primary Examiner—Edward M. Coven
Assistant Examiner—Max F. Hindenburg
Attorney, Agent, or Firm—Birch, Stewart, Kolasch & Birch

[57] ABSTRACT

An endoscope system includes a solid state imaging device having an array of photosensitive cells for producing a video signal associated with an image of an object formed on the array, a color filter having filter segments of cyan and yellow disposed alternately in two-dimensional in association with the array, an illuminating unit for illuminating an object alternately with a first ray including green and a second ray including at least magenta, and a display unit for visualizing the video signal as a color image of the object. This system further includes a control circuit for synchronizing the imaging device with the illuminating unit so as to cause the imaging device to produce a first video signal including green and associated with a first field of a displayed picture while the illuminating unit illuminates the object with the first ray, and to alternately produce second and third video signals including at least red and blue, respectively, and associated with a second field of the displayed picture while the illuminating unit illuminates the object with the second ray, and a video circuit operative in response to the control circuit for forming the first field including green pixels from the first video signal, and forming the second field including red and blue video pixels disposed alternately from the second and third video signals, to cause thereby the fields to be displayed alternately on the display unit.

26 Claims, 32 Drawing Figures

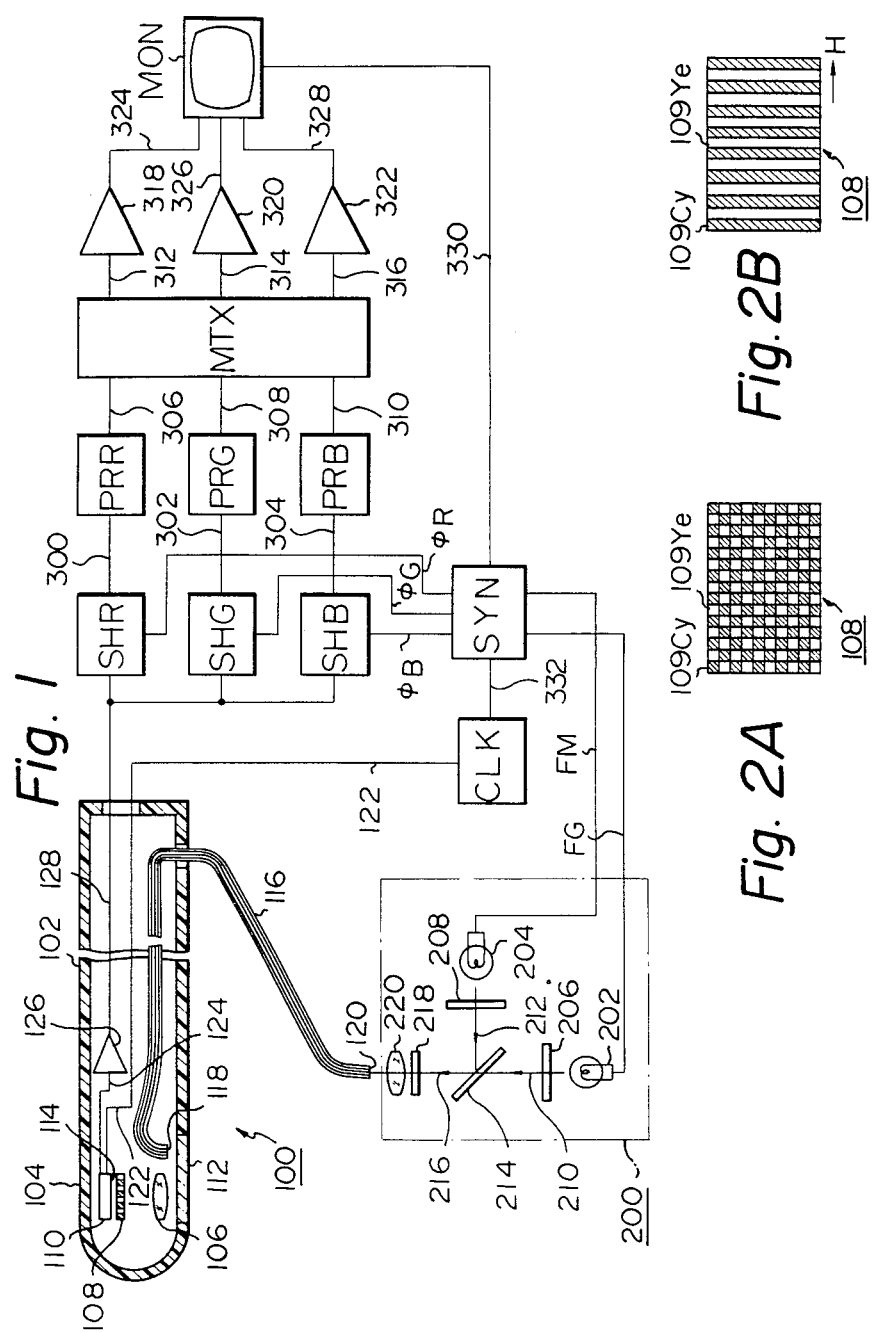

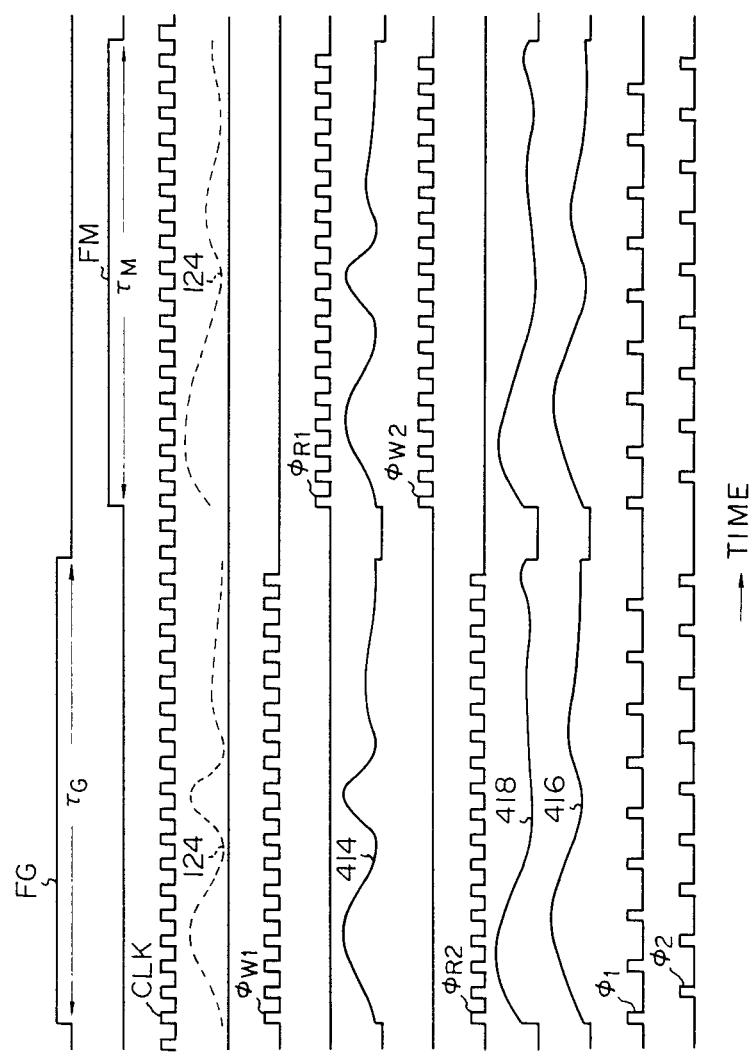

ENDOSCOPE SYSTEM USING SOLID STATE IMAGING DEVICE

BACKGROUND OF THE INVENTION

1. Field of the Invention

The present invention relates to an endoscope system, and, more particularly, to an endoscope system using a solid state imaging device.

2. Description of the Prior Art

In order to observe and record an image of the inside of a cavity or opening of a living body or machinery, a fiberscope was conventionally used. A fiberscope is an endoscope having a viewing head unit, which is to be inserted into an opening of an object of interest, and includes at least an imaging optical system for picking up an image of the inside of the opening, a distal end portion of an image guide including a band of optical fiber for conveying an optical image formed by the imaging optical system to a proximal end thereof, and a distal end portion of a light guide including a band of optical fiber for conveying light to illuminate the inside of the opening. The optical image transmitted over the image guide was observed through a loupe or magnifying glass, photographed by a still camera, or monitored by a television system.

Recent progress in semiconductor technology has brought into use a self-scanning solid state imaging device, such as a charge-coupled device (CCD), for example, in the field of television cameras. In comparison with an image pickup tube, such as a vidicon, included in a conventional television camera, an imaging system using a solid state image sensor may be compactly designed. Thus proposals were made to install such a solid state image sensor in a head unit of an endoscope to convert an optical image of an object into electrical signals, which in turn are transmitted to a cathode-ray tube (CRT) display to be visualized thereon as a television picture. See Japanese Patent Laid-Open Publication No. 65962/1976, for example.

In order to monitor on a CRT a color television picture from an endoscope head unit, the following three techniques may be proposed. First, a fundamental technique is directed to a system including three separate solid state image sensors each for picking up an image of one of the three primary colors, red (R), green (G) and blue (B), formed and separated by an imaging optical system. A second system includes a single solid state imaging device having an array of photosensitive cells, over which is provided is a multi-color filter having color filter segments of the three primary colors, R, G and B, arrayed in association with the photosensitive cells in a mosaic pattern. In a third system, taking account of the specific structural features and of an endoscope and the situations of its use, the inside of a cavity of an object is illuminated with light which is transmitted over a light guide and changes in color cyclically between R, G, and B, so that a single imaging device picks up in time-serial object images of the three primary colors, R, G and B. The illuminating light is produced at the proximal end of the light guide by rotating in front of a light source a disk of color filter having three segments of the primary colors, R, G and B at a predetermined revolutionary speed.

Those systems, however, raise problems in applications of an endoscope. The above first system is fundamental and primitive system, and produces images of satisfactory image quality. It is, however, not possible to provide a small viewing head of an endoscope with such three image sensor systems, which would, if provided, cause the viewing head to be enlarged in size so as not to be insertable into a small cavity as of a living body, and therefore reduces the utility of the endoscope.

In the case of the second system, it is possible to design a head unit of an endoscope in small size. An image picked up by the single image sensor is, however, degraded in resolving power due to a lower number of green picture elements (pixels or pels), which are predominant over the resolving power of the picture, involved in the mosaic color filter having R, G and B elements on the image sensor. Particularly, with a smaller head unit, the imaging device does not include so many photosensitive cells on its imaging surface or array as to maintain a satisfactory image quality. Degradation in resolving power is critical in the case of a small viewing head.

In the aforementioned third system, a sole image sensor is operative in a field-serial fashion to produce three primary-color video signal components in time-serial, so that failure may occur in registration between fields of the three primary colors in the case of an object moving or changing faster. This may also cause degradation in image quality.

SUMMARY OF THE INVENTION

It is therefore an object of the present invention to provide an endoscope system using a solid state imaging device which is free from the aforementioned drawbacks in the prior art systems, and which is configured with the specific structural features and situations of use of an endoscope taken into account.

In accordance with the invention, an endoscope system comprises a solid state imaging device having an array of photosensitive cells for producing a video signal associated with an image of an object formed in the array, a color filter having filter segments of cyan and yellow disposed alternately in two-dimensions in association with the array of photosensitive cells, illuminating means for illuminating an object alternately with a first ray including green and a second ray including at least magenta, and display means for visualizing the video signal as a color image of the object. The system of the present invention further includes a control circuit for synchronizing the operation of the imaging device with the illuminating means so as to cause the imaging device to produce a first video signal including green and associated with a first field of a displayed picture while the illuminating means illuminates the object with the first ray, and to alternately produce second and third video signals including at least red and blue, respectively, and associated with a second field of the displayed picture while the illuminating means illuminates the object with the second ray, and a video circuit operative in response to the control circuit for forming the first field including green pixels from the first video signals produced from the imaging device, and forming the second field including red and blue pixels disposed alternately from the second and third video signals produced from the imaging device, to thereby cause the fields to be displayed alternately on the display means.

In accordance with the invention, an endoscope system comprising the solid state imaging device, color filter, illuminating means, and display means, and the control circuit further comprises first and second storage means each for storing the video signals associated with the entire array of photosensitive cells of the imaging device, and a transferring circuit operative in response to the control circuit for transferring the video signals stored in the storage means and the video signals produced from the imaging device to the display means, the control circuit being operative to cause the video signals produced from the imaging device during a time period of one field to be stored selectively in either one of the storage means and to be transferred by the transferring circuit to the display means. The control circuit simultaneously causes video signals involved in a preceding field stored in the other of the storage means to be read out therefrom and to be transferred by the transferring means to the display means, whereby the first, second and third video signals are displayed on the display means as one field of the image of the object.

BRIEF DESCRIPTION OF THE DRAWINGS

The objects and features of the present invention will become more apparent from a consideration of the following detailed description and the drawings in which:

FIG. 1 is a partially schematic and partially diagramic block diagram showing an embodiment of an endoscope system in accordance with the present invention;

FIGS. 2A and 2B are plan views showing examples of a micro color filter provided in the embodiment shown in FIG. 1;

FIGS. 10A through 10M show the signal waveforms appearing at the portions of the system shown in FIG. 9.

DESCRIPTION OF THE PREFERRED EMBODIMENTS

Figure 3:
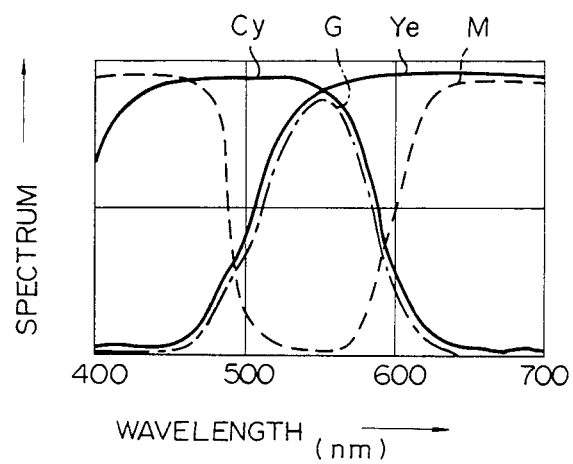
FIGS. 3 through 7 plot the wavelength spectra useful for understanding the principles employed in the invention.

With reference to FIG. 1, an endoscope system includes an endoscope 100 having flexible sheath 102, of which a distal end portion 104 is provided therein with an imaging system including an objective lens 106, a micro color filter 108, and a solid state imaging device 110, which may advantageously be a charge transfer device (CTD), such as a charge coupled device (CCD) and a bucket brigade device (BBD). Distal end portion 104 functions as a viewing head equipped with a viewing window 112, through which objective lens 106 views an object, not shown, to form an image thereof on an array of photosensitive cells 114 of imaging device 110. Viewing head 104 may be inserted into a small cavity or opening of a living body or machinery.

As shown in FIG. 2A, filter 108 has micro filter segments 109Cy and 109Ye of cyan (Cy) and yellow (Ye), respectively, disposed alternately in a mosaic pattern in association with an array of photosensitive cells 114 of image sensor 110. Cyan and yellow segments 109Cy and 109Ye exhibit the wavelength spectra as shown in FIG. 3 by the solid curves Cy and Ye, respectively.

Micro color filter 108 may include, as shown in FIG. 2B, thin stripes of cyan and yellow 109Cy and 109Ye, which are long in the direction perpendicular to the direction H in which the photosensitive cells in the array 114 of sensor 110 are driven horizontally in a raster scanning fashion.

Sheath 102 is for example about two to four meters long, and includes a flexible tubular material to be inserted into a cavity of a living body or machinery.

Sheath 102 is equipped therein with a light guide 116 including a band of optical fiber, of which a distal end is terminated with its surface 118 directed to viewing window 112. This makes it possible to direct a light beam conveyed on and developed from the band of optical fiber 116 to a portion of an object through window 112.

At a proximal end 120 of light guide 116, a light source system 200 is provided which has two flash lamps 202 and 204, which may be turned on and off at a high speed. In front of one lamp 202, a green (G) optical filter 206 is arranged, and in front of the other lamp 204, a magenta (M) filter 208 is disposed. Filters 206 and 208 have the wavelength spectra as shown by a chain curve G and a dotted curve M, respectively, in FIG. 3, for example.

At the crosspoint of optical paths 210 and 212 from lamps 202 and 204, a dichroic filter mirror 214 is provided as depicted in FIG. 1. Dichroic mirror 214 allows the green ray or beam to pass from lamp 202 and the magenta ray or beam to reflect from lamp 204. By means of mirror 214, the green and magenta rays or beams form a common optical path 216.

Figure 5:
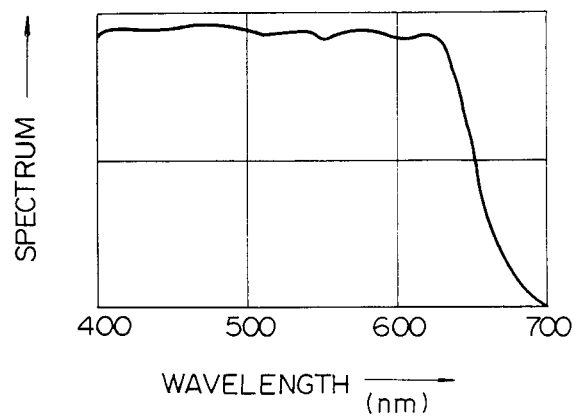

Along optical path 216, there may advantageously be disposed an infrared (IR) cutoff filter 218 and a condensor lens 220, as shown in FIG. 1. Infrared cutoff filter 218 exhibits the wavelength spectrum as shown in FIG. 5, for example. IR cutoff filter 218 thus cuts off rays having longer wavelengths in the infrared region. Condensor lens 220 directs and concentrates the rays emitted from lamps 202 and 204 to an end surface 120 of light guide 116 to cause the rays to be carried into light guide 116. Flash lamps 202 and 204 alternately turn on and off in response to synchronizing signals FG and FM, as discussed later.

Solid state imaging device 110 has a drive input port 122, which is supplied with clocks from clock generator CLK to drive imaging device 110 as described later. Solid state image sensor 110 has a video signal output port 124 connected to a preamplifier 126, which has an output 128 connected in common to sample and hold circuits SHR, SHG and SHB. Those sample and hold circuits SHR, SHG and SHB are driven by sampling clocks $\phi_R$, $\phi_G$ and $\phi_B$ fed from synchronizing circuit SYN, as described later. Sample and hold circuits SHR, SHG and SHB have outputs 300, 302 and 303 connected to inputs to processing circuits PRR, PRG and PRB, respectively.

Processing circuits PRR, PRG and PRB process the color-separated video signals of red (R), green (G) and blue (B), respectively, and may include a conventional automatic gain control (AGC), a lowpass filter, a gamma correction circuit, a blanking circuit and a clipper circuit.

Processing circuits PRR, PRG and PRB have outputs 306, 308 and 310 interconnected to a video matrix network MTX, which may be a conventional circuit for forming intensity and color difference signals under the NTSC standard television format, for example, from the color-separated video signals supplied from processing circuits PRR, PRG and PRB. Matrix network MTX has outputs 312, 314 and 316 connected to videoband amplifiers 318, 320 and 322, respectively, which have outputs 324, 326 and 328 coupled to a monitor unit MON, such as a cathode-ray tube (CRT) display. Monitor unit MON displays in color an image of an object picked up by solid state image sensor 110 in response to the synchronizing signals fed on lead 330 from synchronizing circuit SYN.

Synchronizing circuit SYN generates various synchronous or timing control signals for control over the entire circuits of the system. Synchronizing circuit SYN is supplied with clocks over lead 332 from clock generator CLK.

Now, operations of the system will be described with reference to FIGS. 3 through 8. In FIG. 8, the signal waveforms are designated by the same reference numerals as those of the circuits producing the waveforms or of the connections on which the waveforms are transmitted.

Synchronizing circuit SYN enables clock generator CLK to produce clocks CLK, FIG. 8C on lead 122. Clock CLK has three or two phases which are in fact shifted in phase with each other, but are shown in the figure with simply a single phase for simplicity. Clocks CLK drive solid state image sensor 110. It is also to be noted that those clock pulses are shown for simplicity not by an actual number of pulses in the figure.

Synchronizing circuit SYN produces timing control of synchronizing signals on leads FG and FM as shown in FIGS. 8A and 8B, respectively, to cause flash lamps 202 and 204 to be alternately turned on and off in response thereto. As seen from FIGS. 8A and 8B, the periods of time FG and FM during which the signals are in the high levels thereof are associated with each of the field periods of time involved in the video signals. Lamps 202 and 204 are thus actuated alternately to turn on and off in response to the field periods of time of the video signals.

Suppose now that the synchronizing signal FG becomes high in association with an odd numbered field counted from a certain preceding field, and the synchronizing signal FM becomes high in association with an even numbered field counted from that preceding field.

During an odd numbered field period, when the synchronizing signal FG goes to its high level, flash lamp 202 is turned on to emit a ray, which in turn passes through green filter 206, dichroic filter mirror 214, infrared cutoff filter 218 and condensor lens 220 so as to direct a green ray to light guide 116. The green ray is thus supplied during the period of time $\tau_G$ during which the synchronizing signal is in its high level. An object to be imaged, not shown, is therefore illuminated with the green ray so that objective lens 106 forms a green image of the object on the array of photosensitive cells 114 of solid state imaging device 110 through micro color filter 108.

Figure 6:
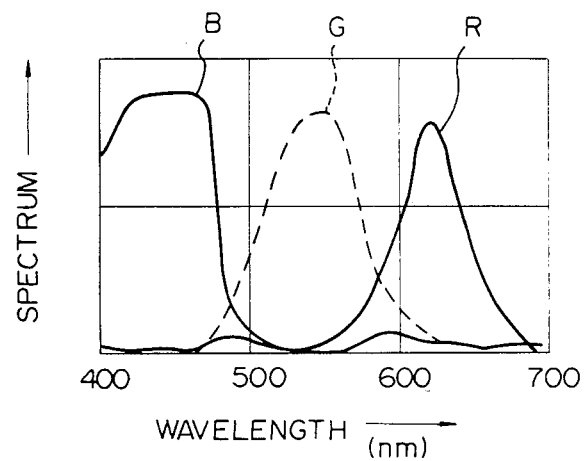

Filter 108 has photosensitive cells associated with cyan segments 109Cy, FIG. 2, i.e. cyan pixels, in the array 114 receive the light having the wavelength spectrum designated by the chain curve G, FIG. 3, through the filter segments having the spectrum designated by the solid curve Cy in the figure so that they produce the electrical signals associated with the wavelength spectrum designated by a dotted curve G, FIG. 6, namely green video signals. The photosensitive cells of the array 114 which are associated with the yellow filter segments of filter 108, i.e. yellow pixels, receive the same green ray through the filter segments having the wavelength spectrum depicted by the solid curve Ye, FIG. 3, so as to produce green video signals corresponding to the spectrum designated by the dotted curve G, FIG. 6. Accordingly, all the photosensitive cells of the array 114 produce in response to the clocks CLK the green video signals serially in time on lead 124. As seen from FIG. 8D, the green signals 124 are modulated in pulse amplitude, that is, they are pulse amplitude modulation (PAM) signals, of which the envelope is shown in the figure by a dotted line 700. The green video signals are amplified by preamplifier 126 to be fed to the inputs to sample and hold circuits SHR, SHG and SHB by way of lead 128.

During an odd numbered field period of time $\tau_G$, sample and hold circuit SHG is supplied with sampling clock $\phi_G$ with a predetermined phase difference maintained with respect to clock CLK as shown in FIG. 8E whereas the remaining sample and hold circuits SHR and SHB are not supplied with the sampling clocks. Therefore, only the sample and hold circuit SHG produces on its output 302 the thus sampled and held green video signals 302, FIG. 8F, which are in turn transmitted to monitor unit MON through matrix network MTX, and amplifiers 318, 320 and 322. The green video signals are then displayed on monitor unit MON as a green visual image. The green signals correspond to the envelope 700, FIG. 8D.

During the successive even numbered field period, synchronizing circuit SYN produces synchronizing signal FM, FIG. 8B, over the period of time $\tau_M$ to enable lamp 204 to turn on during that period of time. The ray emitted from lamp 204 during the period of time runs through magenta filter 208, dichroic filter mirror 214, infrared cutoff filter 218, condensor lens 220 and light guide 116 to illuminate the object.

Figure 4:
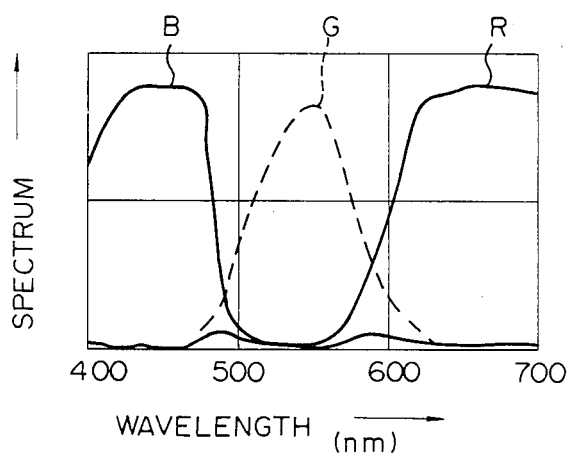

An image of the object under the illumination of the magenta ray is formed through objective lens 106 and micro color filter 108 on the array of photosensitive cells 114 of solid state image sensor 110. The cyan image formed on the array of photosensitive cells 114 has the wavelength spectrum as shown in FIG. 3 by the solid curve Cy, and magenta filter 208 has the spectrum as shown by the dotted curve M in the figure. Accordingly, the electrical signals produced from the cyan pixels of image sensor 110 are the signals associated with the wavelength spectrum designated by the solid line B in FIG. 6, namely, blue video signals. The yellow pixels in the array of photosensitive cells 114 have the wavelength spectrum as shown in FIG. 3 by the dotted curve Ye, and magenta filter 208 exhibits the spectrum designated by the dotted curve M in the figure, as discussed before. In addition, on optical path 216, infrared cutoff filter 218 is inserted which has the wavelength spectrum as shown in FIG. 5. The electrical signals produced from the yellow pixels of the array 114 are therefore the signals associated with the wavelength spectrum as plotted by the solid line R in the figure, that is, red video signals. It is to be appreciated that if infrared cutoff filter 218 is not provided in the system, then the photosensitive cells of image sensor 110 would produce the video signals which have the wavelength spectra as shown in FIG. 4.

Thus, during the even numbered field period of time $\tau_M$, the cyan pixels of imaging device 110 produce blue video signals, and the yellow pixels do red video signals. The photosensitive cells in the array 114 of imaging device 110, when driven by the clocks CLK, FIG. 8C, in a sequential order for raster scanning, the blue and red video signals are produced on output 124 alternately on a time base. The video signals are amplified by amplifier 126 to be fed on lead 128 to the respective sample and hold circuits SHR, SHG and SHB.

Synchronizing circuit SYN generates, as shown in FIGS. 8G and 8I, the sampling clocks $\phi_R$ and $\phi_B$, which are in time with every two pulses of clocks CLK and out of phase with each other by a time difference equal to the period of clocks CLK.

When the first pulse in the sequence of video signal pulses 124 in an even numbered field is a red video signal, then sample and hold circuit SHR is enabled by the first pulse of the sampling clocks $\phi_R$ to produce the red video signal on lead 300. Since the succeeding pulse in the sequence of video signals 124 is associated with blue, sample and hold circuit SHB is enabled by the first pulse of the sampling clocks $\phi_B$ to produce a blue video signal on lead 304. Successively, red and blue video signals are alternately provided to processing circuits PRR, and PRB.

The output waveforms from sample and hold circuits SHR and SHB are shown in FIGS. 8H and 8J, respectively. As clear from the figures, red and blue video signals 300 and 304 correspond with output signals 124 from the imaging device 100 which form an envelope 702 during time period $\tau_M$ which are sampled at every second sampling points. The red and blue video signals 300 and 304 are transferred through processing circuits PRR and PRB, matrix network MTX, and amplifier 318, 320 and 322 to be visualized as red and blue images, respectively, on the screen of monitor unit MON.

In the illustrative embodiment, a green image is displayed on monitor unit MON during an odd numbered field period, and red and blue images ae simultaneously displayed as an array of alternate pixels on monitor unit MON. The color images picked up by solid state image sensor 110 will therefore be displayed on the screen of monitor unit MON.

In the images displayed on monitor unit MON, red and blue images have half as much resolving power as green images. However, since the resolving power of television pictures is dependent upon green video signals, the total color image displayed is not degraded in resolving power. It should also be noted that all color component signals may be obtained from an object during the periods associated with two fields. In comparison with the conventional field serial system in which three color-separated images are picked up in sequence, it takes two thirds the time to complete an entire color image, giving rise to improving registration in time between color-separated images.

The illustrative embodiment includes magenta filter 208. For magenta filter 208, a rotary disk filter may be substituted, which has red and blue filter segments disposed alternately, and is adapted to rotate in response to the clocks supplied from clock generator CLK so that a green illuminating ray is directed during an odd numbered field period, and red and blue illuminating rays are alternately directed during an even numbered field period in timing with scanning of the photosensitive cells of imaging device 110, to light guide 116. Electronic flash bulbs may be applicable alternatively to the flash lamps 202 and 204.

Figure 7:
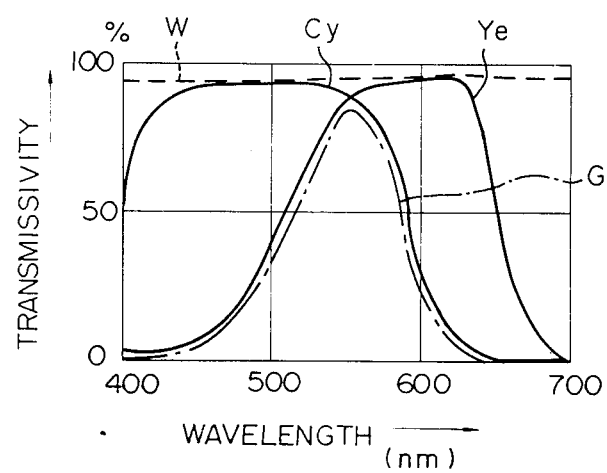
Figure 8:
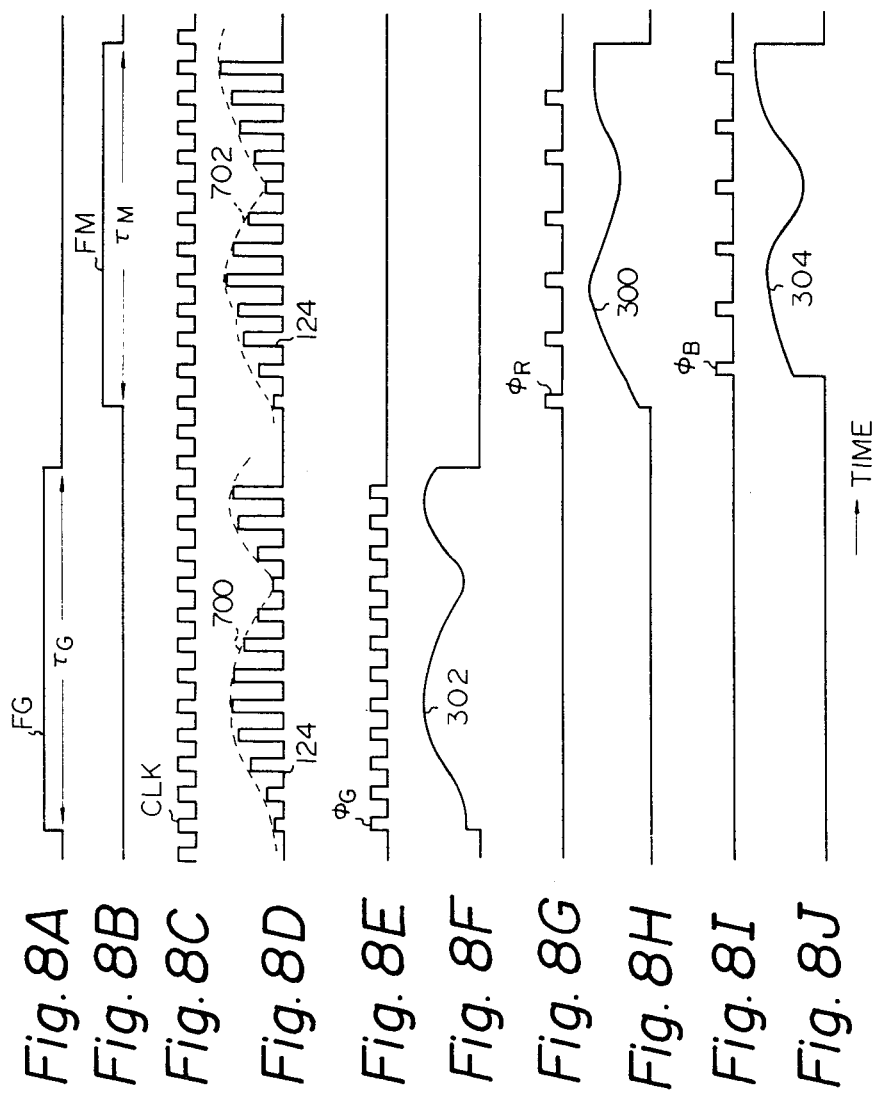
FIGS. 8A through 8J depict the signal waveforms appearing at the portions of the system shown in FIG. 1.

In accordance with the principle of the present invention, color filter 208, FIG. 1, may be a white (W) filter or color temperature correction filter, which is substantially transparent to the wavelengths involved in the entire region as shown in FIG. 7 by the dotted line W, rather than the magenta filter employed in the embodiment described with reference to FIG. 1.

In the alternative embodiment using the W filter as filter 208, green and white rays are transmitted alternately in response to flash lamps 202 and 204 turning on and off under the control of synchronizing circuit SYN to illuminate an object with the alternate green and white rays.

In operation, during an odd numbered field period $\tau_G$, lamp 202 is actuated by synchronizing signal FG to illuminate the object with the green ray so that both cyan and yellow pixels in the array of photosensitive cells 114 produces green electrical signals associated with the spectrum designated by the chain curve G, FIG. 7, since both cyan and yellow filter segments 109Cy and 109Ye have the wavelength spectra designated by the solid lines Cy and Ye in FIG. 7 which have the common band ranging over the green region. This is the same as in the case where the magenta filter is used as filter 208, discussed above.

During an even numbered field period of time $\tau_M$, flash lamp 204 is enabled to emit a ray, which is transmitted through W filter 208 to illuminate the object with the white ray. Therefore, the cyan and yellow pixels in the array of photosensitive cells 114 of image sensor 110 will then produce cyan and yellow video signals corresponding to the wavelength spectra depicted by the solid curves Cy and Ye in FIG. 7. In the illustrative embodiment, infrared cutoff filter 218 is provided on optical path 216 so that the yellow pixels in the photosensitive array 114 produce the video signals associated with the wavelength spectrum of which a portion corresponding to the infrared region is cut off as depicted by the solid curve Ye in FIG. 7.

Accordingly, in the alternative embodiment using a W filter rather than a magenta filter as filter 208, solid state image sensor 110 produces green video signals during an odd numbered field period of time, and cyan and yellow video signals, which will be visualized and disposed in alternate pixels of an image displayed, during an even numbered field period of time. Similarly to the embodiment using a magenta filter, those green, cyan and yellow video signals are in turn sampled and held in sample and hold circuits SHR, SHG and SHB, processed by processing circuits PRR, PRG and PRB, and arranged in video matrix network MTX to be visualized on monitor unit MON as a color picture under the standard NTSC television format, for example.

Figure 9:
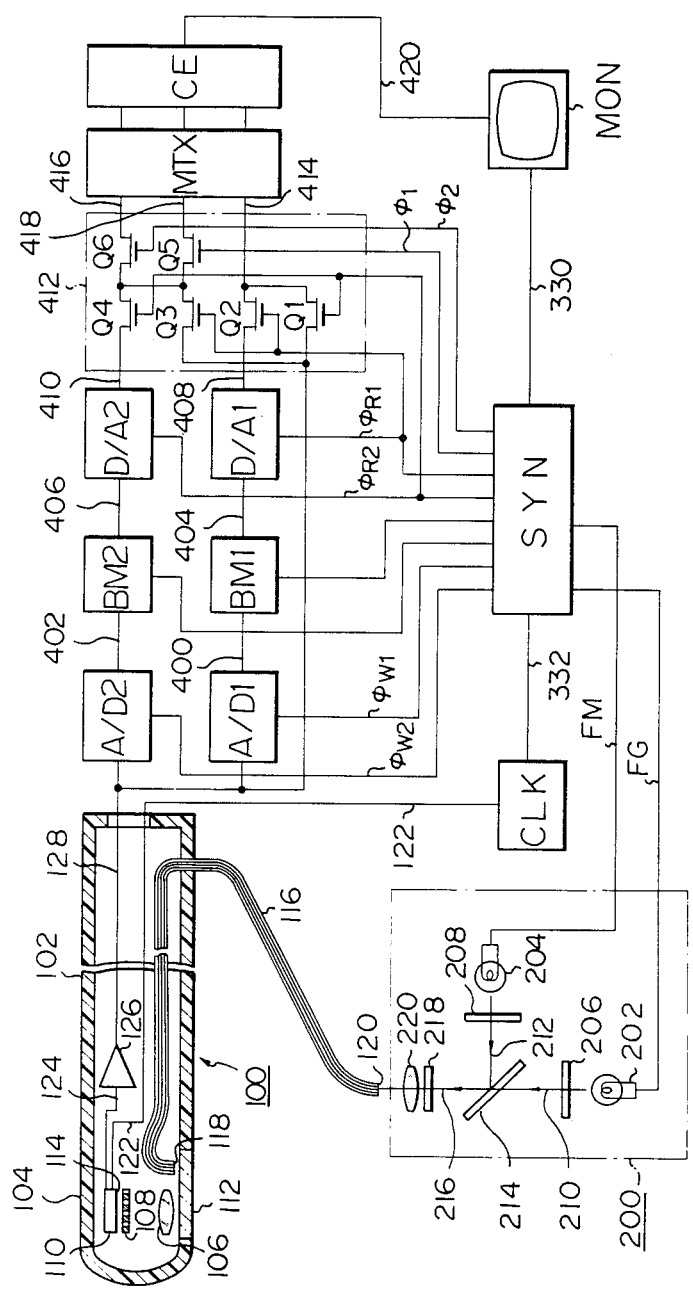
FIG. 9 illustrates in a block diagram another embodiment of an endoscope system in accordance with the invention.

FIG. 9 shows another embodiment of the present invention. In the figure like constituent elements are designated by the same reference numerals as in FIG. 1, and redundant descriptions thereon will be avoided for simplicity.

In the embodiment shown in FIG. 9, preamplifier 126 has output lead 128 interconnected in common to inputs of analog-to-digital (A/D) converters A/D 1 and A/D 2. A/D converters A/D 1 and A/D 2 are responsive to write clocks $\phi_{W1}$ and $\phi_{W2}$, respectively, supplied from synchronizing circuit SYN to convert analog video signals received on input 128 into digital values, which are in turn produced from outputs 400 and 402, respectively.

A/D converters A/D 1 and A/D 2 have outputs 400 and 402 coupled to buffer memories BM1 and BM2, respectively. Buffer memories BM1 and BM2 are a storage in which digital values produced from A/D converters A/D 1 and A/D 2 are temporarily stored, as discussed later, and have each the capacity of storing therein video signal data associated with the pixels involved in one field of an image.

Buffer memories BM1 and BM2 have outputs 404 and 406 connected to digital-to-analog (D/A) converters D/A 1 and D/A 2, respectively. D/A converters D/A 1 and D/A 2 are enabled in response to readout clocks $\phi_{R1}$ and $\phi_{R2}$, respectively, to receive the data stored in buffer storages BM1 and BM2 to convert them into analog signals. D/A converters D/A 1 and D/A 2 have outputs 408 and 410 connected to a switching circuit 412, respectively.

Switching circuit 412 may be of a metal-oxide-semiconductor (MOS) structure, for example, which includes transistor gates Q1 through Q6, as shown in FIG. 9. D/A converter D/A 1 has an output 408 connected to an input 414 to matrix network MTX via the source-drain path of transistor Q2, and D/A converter D/A 2 has an output 410 coupled to an input 416 to matrix network MTX through the source-drain paths of transistors Q4 and Q6. Output 128 of preamplifier 126 is interconnected via the source-drain path of transistor Q1 to input 414 of matrix network MTX on one hand, and through the source-drain paths of transistors Q3 and Q5 to an input 418 of matrix network MTX on the other hand.

The gate electrodes of transistors Q2 and Q3 are interconnected in common to clock $\phi_{R1}$, and the drain electrodes of transistors Q3 and Q4 are also interconnected in common. Both transistors Q1 and Q4 have a gate electrode supplied with clock $\phi_{R2}$ from synchronizing circuit SYN. Transistors Q5 and Q6 have a gate electrode coupled to clocks $\phi_1$ and $\phi_2$, respectively.

Switching circuit 412 has three outputs 414, 418 and 416 interconnected to an input to a color encoder CE by way of matrix network MTX. Color encoder CE has an output 420 connected to monitor unit MON.

In operation, with reference to FIG. 10, during an odd numbered field period of time a green video signal 124, the left half portion in FIG. 10D, formed by solid state image sensor 110 during a time period $\tau_G$ is amplified by preamplifier 126 to be produced over lead 128 to the inputs to A/D converters A/D 1 and A/D 2. During the period of $\tau_G$, as shown in FIG. 10E, only A/D converter A/D 1 is operative in response to the readout clock $\phi_{W1}$ so that it receives the green video signal to convert it into a digital signal associated therewith, which is in turn stored in buffer storage BM1.

During the successive even numbered field period of time $\tau_M$, solid state imaging device 110 produces alternately red and blue video signals, the right half portion in FIG. 10D, on the lead 124, which signals are in turn received by the inputs to A/D converters A/D 1 and A/D 2. During the period $\tau_M$, only the A/D converter A/D 2 receives the write clock $\phi_{W2}$, FIG. 10H, causing the red and blue video signals to be converted into digital signals through A/D converter A/D 2, the latter signals being stored in buffer memory BM2. The red and blue video signals on the lead 128 are also supplied directly to switching circuit 412.

During an even numbered field period of time $\tau_M$, a readout clock $\phi_{R1}$, FIG. 10F, is fed to D/A converter D/A 1, and the gate electrodes of transistors Q2 and Q3. Thus, the green video signal stored in buffer memory BM1 is sequentially read out therefrom to be converted into an analog signal through D/A converter D/A 1 to be transferred through transistor Q2 to lead 414. The output waveforms on lead 414 are shown in the right half portion of FIG. 10G. In addition, the red and blue video signals fed then directly from lead 128 to switching circuit 412, as discussed above, are transmitted via transistor Q3, which is enabled by clock $\phi_{R1}$, to transistors Q5 and Q6.

Transistors Q5 and Q6 are alternately enabled by clocks $\phi_1$ and $\phi_2$, shown in FIGS. 10L and 10M, respectively. It will be recalled that clocks $\phi_1$ and $\phi_2$ are in time with every two pulses of clock CLK, FIG. 10C, with the phase difference therebetween maintained equal to one period of the clock CLK. Assuming that the first pulse of the red and blue video signals is associated with a red signal, the red video signal is produced on lead 418 when transistor Q5 is enabled in response to the first pulse of clock $\phi_1$, and successively the blue video signal is produced on lead 416 when transistor Q6 is enabled in response to the first pulse of clock $\phi_2$. Subsequently, as transistors Q5 and Q6 are alternately enabled by clocks $\phi_1$ and $\phi_2$, respectively, red and blue video signals are produced on outputs 418 and 416. Those output waveforms on leads 418 and 416 are shown in the right halves of FIGS. 10J and 10K, respectively.

Thus, during an even numbered field period of time, a green video signal, FIG. 10G, for the immediately preceding odd numbered field is produced on lead 414, while red and blue video signals, FIGS. 10J and 10K, for that even numbered field are produced on leads 418 and 416, respectively. Those produced video signals are composed in matrix circuit MTX into a composite color television signal to be visualized on the screen of monitor unit MON as a color picture of that even numbered field.

During the succeeding odd numbered field period of time, the red and blue video signals stored in buffer storage BM2 during the immediately preceding even numbered field period are read out therefrom by D/A converter D/A 2 in response to readout clock $\phi_{R2}$, FIG. 10I, to be converted into analog signals, which are in turn produced on lead 410. A green video signal is produced on lead 128, on the other hand, which is formed during that odd numbered field from image sensor 110 through amplifier 126. The green video signal is transferred via A/D converter A/D 1 to buffer storage BM1 to be stored therein, as well as to switching circuit 412 directly. Clock $\phi_{R2}$ is also supplied to transistors Q1 and Q4 of switching circuit 412 so that the green signal on lead 128 passes transistor Q1 to lead 414. The signal waveform on lead 414 is shown in the left part of FIG. 10G.

The red and blue video signals read out on lead 410, which signals are associated with the immediately preceding even field, are transferred through transistor Q4 enabled by clock $\phi_{R2}$. Among the output signals from transistor Q4, the red signal is transferred to lead 418 by transistor Q5 enabled by clock $\phi_1$, and the blue video signal is transferred to lead 416 by transistor Q6 enabled by clock $\phi_2$. The signal waveforms on leads 418 and 416 are shown in the left portions of FIGS. 10J and 10K, respectively. Matrix circuit MTX composes the green, red and blue video signals into a composite color television signal, which is in turn visualized on the screen of monitor unit MON as a color image of that odd field.

In the embodiment described with reference to FIG. 1, since green images picked up under a green illumination, and red and blue images formed under a magenta illumination are alternately displayed on the screen of monitor unit MON, flickers in color may sometimes occur in the images on the screen, annoying a viewer. In the embodiment shown in FIG. 9, however, such flickers will not appear in the displayed images since green images formed under a green illumination are simultaneously visualized as a single field on the screen together with red and blue images picked up under a magenta illumination. As in the case of the embodiment described with reference to FIG. 1, filter 208 may be a W filter, i.e. a color temperature correction filter, instead of a magenta filter so as to cause the photosensitive cells in the array 114 associated with cyan and yellow filter segments 109Cy and 109Ye to produce green video signals, and cyan and yellow video signals in response to green and white rays, respectively.

In accordance with the invention, an endoscope system includes a single solid state image sensor to produce on a display screen images which are, in comparison with the prior art system, improved in resolving power, registration in time, and image quality. Micro color filter 108 provided in front of photosensitive array 114 includes only two-color segments, rather than three-color segments employed in the prior art, to be manufactured more easily. The illuminating system conveys two-color rays, being simpler in structure. Accordingly, a system in accordance with the invention is advantageously applicable to an endoscope, which is required compact in structure, with a higher resolving power maintained, as is one of the important features on the NTSC standard television format.

While the present invention has been described in terms of specific illustrative embodiments, it is to be appreciated to be susceptible of modification by those skilled in the art within the spirit and scope of the appended claims.

What is claimed is:

1. An endoscope system for developing an image of an object comprising:
   solid state imaging means having an array of photosensitive cells for producing video signals associated with the image of an object as formed on said array;
   a color filter disposed between the object and said array of photosensitive cells and consisting essentially of alternately and two-dimensionally disposed filter segments of cyan and yellow;
   illuminating means for illuminating the object alternately with a first beam of green light and a second beam of magenta light;
   video display means for visualizing the image of the object in color from said video signals produced by said solid state imaging device;
   control circuit means for synchronizing the video signals produced by said imaging means in conjunction with said illuminating means to cause said imaging means to produce a first video signal including green information and associated with a first field of a displayed image when said illuminating means illuminates the object with the first beam, and to produce alternately second and third video signals including at least red and blue information, respectively, and associated with a second field of the displayed image when said illuminating means illuminates the object with the second beam; and
   video circuit means, responsive to said control circuit means, for forming the first field including green pixels from the first video signal, and the second field including red and blue pixels disposed alternately from the second and third video signals, said video circuit means driving said video display means to visualize the first and second fields alternately.

2. A system in accordance with claim 1, wherein said illuminating means comprises first and second light emitting means operative in response to said control means for alternately emitting beams having a differing spectra, a first optical filter associated with said first light emitting means for passing the first beam, a second optical filter associated with said second light emitting means for passing the second beam, and means for directing the first and second beams, after passing said first and second optical filters, respectively, to the object.

3. A system in accordance with claim 2, wherein said first optical filter comprises a green filter, said second optical filter comprising a magenta filter.

4. A system in accordance with claim 2, wherein said means for directing the first and second beams comprises an infrared cutoff filter for removing infrared from the first and second beams having passed said first and second optical filters, respectively.

5. A system in accordance with claim 1, wherein said filter segments of cyan and yellow are arranged in a mosaic pattern.

6. A system in accordance with claim 1, wherein said filter segments of cyan and yellow are arranged in stripes which are long in the direction perpendicular to a horizontal scanning direction of the array of photosensitive cells when the array is scanned in a raster fashion.

7. A system in accordance with claim 1 further comprising casing means including a flexible and elongated sheath and a head portion to be inserted into an opening for enclosing therein said solid state imaging device and said color filter, said illuminating means comprising optical fiber for conveying the first and second rays to the head portion.

8. An endoscope system for developing an image of an object comprising:
   solid state imaging means having an array of photosensitive cells for producing video signals associated with the image of an object as formed on said array;
   a color filter disposed between the object and said array of photosensitive cells and consisting essentially of alternately and two-dimensionally disposed segments of cyan and yellow;
   illuminating means for illuminating the object alternately with a first beam of green light and a second beam of magenta light;
   video display means for visualizing the image of the object in color from said video signals produced by said solid state imaging device;
   control circuit means for synchronizing the video signals produced by said imaging means in conjunction with said illuminating means to cause said imaging means to produce a first video signal including green information and associated with a first field of a displayed image when said illuminating means illuminates the object with the first beam, and to produce alternately second and third video signals including at least red and blue information, respectively, and associated with a second field of the displayed image when said illuminating means illuminates the object with the second beam;
   first and second storage means, each for storing therein the video signals produced by said imaging means; and transfer circuit means, responsive to said control circuit means, for transferring the video signals stored in said storage means and the video signals produced by said imaging means to said video display means;

said control circuit means controlling said first and second storage means and transfer circuit means to cause the video signals produced from said imaging means and associated with said first field to be selectively stored in said first storage means and to be transferred to said video display means, and simultaneously to cause the video signals stored in said second storage means associated with the second field to be read out from said second storage means and transferred to said video display means, thereby to visualize the first, second and third video signals on said display means as a single field.

9. A system in accordance with claim 8, wherein said transfer circuit means comprises means responsive to said control circuit means for separating the second video signal from the third video signal when read from either one of said first and second storage means.

10. A system in accordance with claim 8, wherein said illuminating means comprises first and second light emitting means operative in response to said control means for emitting beams alternately to each other, a first optical filter associated with said first light emitting means for passing the first beam, a second optical filter associated with said second light emitting means for passing the second beam, and means for directing the first and second beams after passing said first and second optical filters, respectively, to the object.

11. A system in accordance with claim 10, wherein said first optical filter comprises a green filter, said second optical filter comprising a magenta filter.

12. A system in accordance with claim 10, wherein said means for directing the first and second beams comprises an infrared cutoff filter for removing infrared from the first and second beams after passing said first and second optical filters, respectively.

13. A system in accordance with claim 8, wherein said filter segments of cyan and yellow are arranged in a mosaic pattern.

14. A system in accordance with claim 8, wherein said filter segments of cyan and yellow are arranged in stripes which are long in the direction perpendicular to a horizontal scanning direction of the array of photosensitive cells when the array is scanned in a raster fashion.

15. A system in accordance with claim 8 further comprising casing means including a flexible and elongated sheath and a head portion to be inserted into an opening for enclosing therein said solid state imaging device and said color filter, said illuminating means comprising optical fiber for conveying the first and second beams to said head portion.

16. An endoscope system for developing an image of an object comprising:
solid state imaging means having an array of photosensitive cells for producing video signals associated with the image of an object as formed on said array;
a color filter disposed between the object and said array of photosensitive cells and consisting essentially of alternately and two-dimensionally disposed filter segments of cyan and yellow;
means for alternately illuminating the object with a first beam of green light and second beam of white light;
video display means for visualizing the image of the object in color from said solid state imaging device;
control circuit means for synchronizing the video signals produced by said imaging means in conjunction with said illuminating means to cause said imaging means to produce a first video signal including green information and associated with a first field of a displayed image when said illuminating means illuminates the object with said first beam, and to alternately produce second and third video signals including at least yellow and cyan information, respectively, and associated with a second field of the displayed image when said illuminating means illuminates the object with the second beam; and
video circuit means, responsive to said control circuit means, for forming the first field including green pixels from the first video signal, and the second field including alternately disposed cyan and yellow pixels from said second and third video signals, said video circuit means driving said video display means to visualize said first and second fields alternately.

17. A system in accordance with claim 16, wherein said illuminating means comprises first and second light emitting means operative in response to said control means for alternately emitting beams having differing spectra, a first optical filter associated with said first light emitting means for passing the first beam, a second optical filter associated with said second light emitting means for passing the second beam, and means for directing the first and second beams, after passing said first and second optical filters, respectively, to the object.

18. The system of claim 2 wherein said first optical filter comprises a green filter, said second optical filter comprising only a color temperature correction filter.

19. A system in accordance with claim 16, wherein said filter segments of cyan and yellow are arranged in a mosaic pattern.

20. A system in accordance with claim 16, wherein said filter segments of cyan and yellow are arranged in stripes which are long in the direction perpendicular to a horizontal scanning direction of the array of photosensitive cells when the array is scanned in a raster fashion.

21. An endoscope system for developing an image of an object comprising:
solid state imaging means having an array of photosensitive cells for producing video signals associated with the image of an object as formed on said array;
a color filter disposed between the object and said array of photosensitive cells and consisting essentially of alternately and two-dimensionally disposed filter segments of cyan and yellow;
means for alternately illuminating the object with a first beam of green light and a second beam of white light;
video display means for visualizing the image of the object in color from said video signals produced by said solid state imaging device;
control circuit means for synchronizing the video signals produced by said imaging means in conjunction with said illuminating means to cause said imaging means to produce a first video signal including green and associated with a first field of a displayed image when said illuminating means illuminates the object with the first beam, and to alternately produce second and third video signals including at least yellow and cyan, respectively, and associated with a second field of the displayed image when said illuminating means illuminates the object with the second beam;

first and second storage means, each for storing video signals produced by said imaging means therein; and transfer circuit means, responsive to said control circuit means, for transferring the video signals stored in said storage means and the video signals produced by said imaging means to said video display means;

said control circuit means controlling said first and second storage means and transfer circuit means to selectively store the video signals produced from said imagingmeans and associated with said first field in said first storage means and to transfer said video signals to said display means, and simultaneously to read out the video signals stored in said second storage means and transfer them to said visual display means, to thereby visualize the first, second and third video signals on said display means as a single field.

22. A system in accordance with claim 21, wherein said transfer circuit means comprises means responsive to said control circuit means for separating the second video signal from the third video signal when read from either one of the said first and second storage means.

23. A system in accordance with claim 21, wherein said illuminating means comprises first and second light emitting means operative in response to said control means for emitting beams alternately to each other, a first optical filter associated with said first light emitting means for passing the first beam, a second optical filter associated with said second light emitting means for passing the second beam, and means for directing the first and second beams after passing said first and second optical filters, respectively, to the object.

24. The system of claim 23 wherein said first optical filter comprises a green filter and said second optical filter comprises only a color temperature correction filter.

25. A system in accordance with claim 21, wherein said filter segments of cyan and yellow are arranged in a mosaic pattern.

26. A system in accordance with claim 21, wherein said filter segments of cyan and yellow are arranged in stripes which are long in the direction perpendicular to a horizontal scanning direction of the array of photosensitive cells when the array is scanned in a raster fashion.

* * * * *